US006284873B1

(12) United States Patent
Mikolajczyk et al.

(10) Patent No.: US 6,284,873 B1
(45) Date of Patent: Sep. 4, 2001

(54) COMPLEX OF HUMAN KALLIKREIN 2 (HK2) AND PROTEASE INHIBITOR-6 (PI-6) IN PROSTATE TUMOR TISSUE AND METHODS OF USING THE COMPLEX

(75) Inventors: Stephen D. Mikolajczyk; Mohammad S. Saedi, both of San Diego, CA (US)

(73) Assignee: Hybritech Incorporated, San Diego, CA (US)

( * ) Notice: Subject to any disclaimer, the term of this patent is extended or adjusted under 35 U.S.C. 154(b) by 0 days.

(21) Appl. No.: 09/266,957

(22) Filed: Mar. 12, 1999

(51) Int. Cl.[7] ..................... C07K 14/81; C07K 14/435; G01N 33/53; G01N 33/48
(52) U.S. Cl. ............... 530/402; 530/350; 530/828; 435/7.1; 436/63; 436/64
(58) Field of Search ....................... 530/350, 402, 530/828; 435/7.1; 436/63, 64

(56) References Cited

PUBLICATIONS

Grauer, Lana S et al "Detection of Human Glandular Kallikrein, hK2, as its Precursor Form and in Complex with Protease Inhibitors in Prostate Carcinoma Serum.". Abtract of Journal of Andrology Jul.–Aug., 1998vol. 19, No. 4, Jul. 1998 (Jul. 1998), pp. 407–411, XP000907357 ISSN: 0196–3635.

Scott, Fiona L et al "Proteinase Inhibitor 6 (PI–6) expression in Human Skin: Induction of PI–6 and a PI–6/Proteinase Complex During Keratinocyte Differentiation." Abstract of Experimental Cell Research Dec. 15, 1998, vol. 245, No. 2, Dec. 15, 1998 (Dec. 15, 1998), pp. 263–271, XP002138676, ISSN: 0014–4827.

Coughlin, Paul et al "Cloning and Molecular Characterization of a Human Intracellular Serine Proteinase Inhibitor." Abtract of Proceedings of the national Academy of Sciences of the United Staes of America 1993, vol. 90, No. 20, 1993, pp. 9417–9421, XP002138677 ISSN: 0027–8424.

Mikolajczyk, Stephen D. et al :Identification of a Novel Complex Between Human Kallikrein 2 and Protease Inihibitor–6 in Prostate Cancer Tissue. Cancer Research Aug. 15, 1999, vol. 59, No. 16, Aug. 15, 1999 (Aug. 15, 1999), pp. 3927–3930, XP002138678 ISSN: 0008–5472—the whole document.

Mikolajczyk, Stephen D. et al :Identification of a Novel Complex of Human Kallikrein 2 (hK2) and Protese Inhibitor–6 (PI6) in Prostate Cancer Tissues. copyright, Proceedings of the American Association for Cancer Research Annual Meeting Mar., 1999. XP–002138675, ISSN: 0197–016X—the whole document.

Morgenstern, K.A., et al. "Isolation and characterization of an intracellular serine proteinase inhibitor from a monkey kidney epithelial cell line", J. Biol. Chem., 268: 21560–21568, 1993.

Scott, F.L., et al., "Proteinase inhibitor 6 cannot be secreted, which suggests it is a new type of Cellular serpin", J. Biol. Chem., 271: 1605–1612, 1996.

Morganstern, K.A., et al., "Complementary DNA cloning and kinetic characterization of a novel Intracellular serine proteinase inhibitor: mechanism of action with trypsin and factor Xa as model Proteinases", Biochemistry, 33: 3432–3441, 1994.

Riewald, M., et al., "Identification and characterization of the cytoplasmic antiproteinase (CAP) in human platelets. Evidence for the interaction of CAP with endogenous platelet proteins", J. Biol. Chem., 271: 7160–7167, 1996.

Coughlin, P., et al., "Cloning and molecular characterization of a human intracellular serine Proteinase inhibitor", Proc. Natl. Acad. Sci. U.S.A., 90: 9417–9421m 1993.

Sprecher, C.A., et al., "Molecular cloning, expression, and partial characterization of two novel Members of the ovalbumin family of serine proteinase inhibitors", J. Biol. Chem., 270: 29854–29861, 1995.

Riewald, M. and Schleff, R.R.. "Human cytoplasmic antiproteinase neutralizes rapidly and efficiently Chymotrypsin and trypin–like proteases utilizing distinct reactive site residues", J. Biol. Chem., 271: 14526–14532, 1996.

Helmuth Hilz, et al., "Molecular Heterogeneity of Free PSA in Sera of Patients with Benign and Maglignant Prostate Tumors", Eur. Urol. 1999; 36: 286–292.

*Primary Examiner*—Anthony C. Caputa
*Assistant Examiner*—Anne L. Holleran
(74) *Attorney, Agent, or Firm*—William H. May; Gary T. Hampson

(57) ABSTRACT

The present invention provides a novel complex of hK2 and PI-6 and methods of using the novel complex. The novel complexes of hK2 and PI-6 of the present invention exist at an elevated level in prostate cancer tissues. Therefore, the hK2-PI6 complexes of the present invention may be used as a serum marker for detecting prostate cancer. They may also be used as an immunohistological marker to detect prostate cancer tissues. In accordance with the present invention, the hK2-PI6 complexes of the present invention may be detected in patient tissue samples by immunohistochemical and/or in patient fluid samples by in vitro immunoassay procedures. Diagnostic kits and diagnostic methods for detecting the existence of prostate cancer are also provided.

5 Claims, 4 Drawing Sheets

| kDa | | | N-TERMINAL SEQUENCE | %hK2 |
|---|---|---|---|---|
| 94 — | ▭ | −6 | ACT 1-9; hK2 1-9 | 2% |
| 68 — | ▬ | −5 | hK2 1-9 | 2% |
| 50 — | ▬ | −4 | hK2 146-155 | 10% |
| 33 — | ▬ | −3 | hK2 1-9 | 13% |
| 22 — | ▬ | −2 | hK2 1-9 | 84% |
| 10 — | ▬ | −1 | hK2 146-155 | 73% |

WESTERN BLOT OF PROSTATE TISSUE EXTRACTS PROBED
WITH RABBIT ANTI-PI6 POLYCLONAL ANTIBODIES

COMPLEX OF HUMAN KALLIKREIN 2 (HK2) AND PROTEASE INHIBITOR-6 (PI-6) IN PROSTATE TUMOR TISSUE AND METHODS OF USING THE COMPLEX

BACKGROUND OF THE INVENTION

1. Field of the Invention

The invention relates generally to the prostate and specifically to a novel complex of hK2 and PI-6 formed in the prostate, and methods of using the novel complex.

2. Description of the Prior Art

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Three members of the human kallikrein family have been identified so far, designated hK1, hK2 and hK3 (1). All are serine proteases with high sequence identity. Two of these kallikreins, hK2 and hK3, are found almost exclusively in the prostate (extensively reviewed in (2). hK3, known more commonly as prostate-specific antigen, PSA, is a widely used serum marker for prostate. More recently, hK2 has become the focus of investigations into its possible role as a prostate cancer marker, as well as possible roles in prostate cancer biology (2).

hK2 is similar to PSA in many respects such as prostate tissue localization (3; 4), 80% sequence identity (5; 6), and regulation by androgens (7; 8). From a biochemical perspective, hK2 is different from PSA in that it shows a strong trypsin-like activity while PSA has weak chymotrypsin-like activity. However, unlike true kallikreins, hK2 shows little or no kininogenase-like activity (9; 10) and so does not appear to function primarily as a prostatically-expressed kininogenase.

The physiological roles for hK2 have not been established, though several activities have been described. hK2 has been shown to activate the zymogen form of PSA (pPSA) (11–13), and the zymogen of hK2 (autoactivation) (14). In this respect hK2 is unique from the other human tissue kallikreins, hK1 and PSA. The activation of pPSA by hK2 is particularly interesting since it suggests a possible physiological role for hK2 in the regulation of PSA activity.

Immunohistochemical studies using hK2-specific monoclonal antibodies have shown hK2 to be more highly expressed in prostate carcinoma than in normal tissues (15). This is the inverse of PSA which tends to be lower in more poorly differentiated cancer epithelium than in normal tissues.

hK2 has been shown to activate urokinase-type plasminogen activator (uPA) by cleavage of the single-chain uPA at $Lys^{158}$ to generate the two-chain active form of uPA (12; 16). It has been recently reported that hK2 rapidly complexes with PAI-1 in vitro and that hK2 also inactivates about 6 moles of PAI-1 during complex formation (17). It is therefore possible that the elevated levels of hK2 in prostate cancer play a biological role either by the activation of urokinase or by the inactivation of PAI-1, the primary inhibitor of urokinase.

Physiologically hK2 has been identified as a complex with ACT in serum (18) and PCI in seminal plasma (19). However, it was not previously known whether hK2 forms any tissue specific complex in the prostate. The physiological and biological role of hK2 in the prostate was also not known. Therefore, a need exists to study the role of hK2 in the prostate, particularly in prostate cancer.

SUMMARY OF THE INVENTION

The present invention is based on the discovery of a complex in prostate tissue extracts consisting of hK2 and a serine protease inhibitor known as protease inhibitor-6 (P-6). PI-6 was first reported in placental tissue where it was called placental thrombin inhibitor due to its ability to form in vitro complex with thrombin (20). It has also been called CAP, cytoplasmic antiprotease, since it has been shown to be cytoplasmically localized (21). PI-6 is expressed in epithelial and endothelial cells and has been described in a number of human tissues and cells including kidney, heart, skeletal muscle and platelets (22–24). It has not been reported in the prostate. In all cases so far PI-6 appears to be cytoplasmically localized.

The discovery of hK2-PI6 complex in the prostate is unique from the previous reports of hK2-ACT and hK2-PCI in at least two major respects: 1) PI-6 itself is a novel and relatively newly described member of the serine protease inhibitor family which has not been reported in prostate tissues; and 2) PI-6 is thought to be intracellular, which suggests either a novel pathway for the formation with the putatively extracellular hK2, or an altered pathway, possibly due to the oncogenic process.

While not wanting to be bound by the theory, it is believed that the finding of prostatic PI-6 in complex with hK2 suggests that PI-6 may play certain roles in the prostate. PI-6 represents a tissue-specific inhibitor of hK2 which may have biological significant in the regulation of hK2, and may play a role in prostate cancer biology.

It is a discovery of the present invention that the hK2-PI6 complex is elevated in prostate tumor compared to benign or normal prostate tissue. It is also a discovery of the present invention that the level of PI-6 is elevated in prostate tumor. Therefore, both the complex and the level of hK2 or PI-6 alone may be a novel marker for prostate cancer.

Accordingly, one aspect of the present invention provides an isolated and substantially pure complex consisting of protease inhibitor-6 (PI-6) and human kallikrein 2 (hK2). The hK2 contained in the complex may be an intact hK2 or a fragment of hK2. The complex of the present invention exists at an elevated level in a prostate tumor tissue.

Another aspect of the present invention provides an antibody that is specifically immunoreactive with a complex consisting of protease inhibitor-6 (PI-6) and human kallikrein 2 (hK2). The antibody may be a polyclonal antibody or a monoclonal antibody.

A further aspect of the present invention provides a method of detecting or determining in a sample a complex consisting of protease inhibitor-6 (PI-6) and human kallikrein 2 (hK2). The method comprises the steps of.

(a) contacting an amount of an agent which specifically binds to the complex to be detected with the sample under a condition that allows the formation of a ternary complex comprising the agent and the hK2-PI6 complex; and (b) detecting or determining the presence or amount of the ternary complex.

In preferred embodiments, the agent comprises an antibody. The sample to be detected may be a mammalian tissue sample, particularly a prostate tissue sample, or a sample of human physiological fluid including, but not limited to, serum, seminal plasma, urine, and blood.

Yet another aspect of the present invention provides an immunoassay for detecting hK2-PI6 complexes in a biological fluid sample. The immunoassay comprises the steps of:

(a) providing a first antibody that recognizes one epitope of the hK2-PI6 complex, and a second antibody that recognizes another epitope of the hK2-PI6 complex, (b) contacting the first antibody with the sample under a condition that allows the first antibody to bind to the complex to form a first complex that comprises the first antibody and the hK2-PI6 complex, (c) contacting the second antibody with the first complex under a condition that allows the second antibody to bind to the hK2-PI6 complex to form a second complex that comprises the first antibody, the second antibody and the hK2-PI6 complex, and (d) detecting and determining the second complex as a measurement of the hK2-P16 complex contained in the sample.

According to embodiments of the present invention, the first and second antibodies are respectively an antibody that is specifically immunoreactive for the hK2-PI6 complex. Alternatively, one of the first antibody and second antibodies is an antibody against hK2, and another of the first and second antibodies is an antibody against PI-6.

A further aspect of the present invention provides a diagnostic kit for detecting or determining in a sample a complex consisting of PI-6 and hK2. The kit comprises a known amount of an agent which specifically binds to the complex, wherein the agent is detectably labeled or binds to a detectable label.

According to embodiments of the present invention, the sample is a sample of human physiological fluid or a human prostate tissue sample and the agent comprises an antibody that specifically binds to the complex.

The present invention also provides a diagnostic kit for detecting or determining in a sample a complex consisting of PI-6 and hK2. The kit comprises a known amount of a first agent which specifically binds to the complex, wherein the first agent is detectably labeled or binds to a detectable label, and a known amount of a second agent which specifically binds to the complex, wherein the second agent is bound to a solid support.

According to embodiments of the present invention, the first agent comprises an antibody that is specifically immunoreactive with the complex, and the second agent comprises an antibody that is specifically immunoreactive with the complex. Alternatively, one of the first and second agents comprises an antibody that is specifically immunoreactive with hK2, and another of the first and second agents comprises an antibody that is specifically immunoreactive with PI-6.

The present invention further provides a diagnostic method for determining the presence or absence of prostate cancer comprising:

(a) contacting an amount of an agent, which specifically binds to a complex consisting of PI-6 and hK2, with a sample obtained from a human containing the complex under a condition sufficient to allow the formation of a ternary complex comprising the agent, the PI-6, and the hK2; and (b) determining the amount of the ternary complex in the sample and correlating the amount of the ternary complex to the presence or absence of prostate cancer in the human.

According to embodiments of the present invention, the sample is a sample of physiological fluid or a prostate tissue sample. The agent comprises an antibody.

The present invention further provides a diagnostic method for determining the presence or absence of prostate cancer. The method comprises:

(a) contacting an amount of an agent, which specifically binds to PI-6, with a sample obtained from a human containing the PI-6 under a condition sufficient to allow the formation of a binary complex comprising the agent and the PI-6, wherein the sample is selected from a group consisting of a prostate tissue sample, serum, seminal plasma, urine and blood; and (b) determining the amount of the complex in the sample and correlating the amount of the complex to the presence or absence of prostate cancer in the human.

According to embodiments of the present invention, the sample is a prostate tissue sample, and the agent comprises an antibody.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

Figure 1:
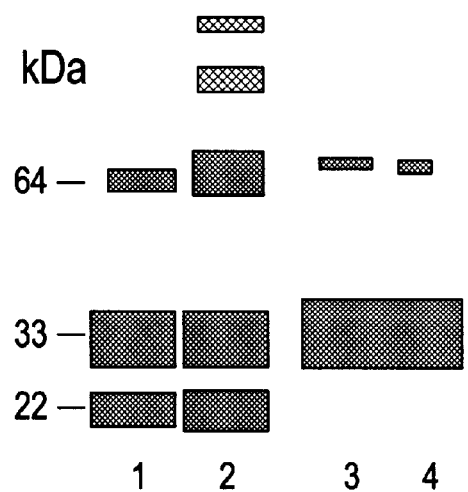
FIG. 1 shows a Western blot of prostate tissue extracts. This figure shows an example of higher hK2-PI6 complex in tumor tissue than benign.

One aspect of the present invention provides an isolated and substantially pure complex consisting of protease inhibitor-6 (PI-6) and human kallikrein 2 (hK2). The term "substantially pure," as used herein, refers to a complex, which consists of protease inhibitor-6 (PI-6) and human kallikrein 2 (hK2), that is substantially free of other proteins, lipids, carbohydrates or other materials with which it is naturally associated. The substantially pure hK2-PI6 complex of the present invention will yield a single major band on a non-reducing polyacrylamide gel. The complex has a molecular weight of about 64 kDa measured by SDS-PAGE technique. The purity of the specific form of hK2 can also be determined by amino-terminal amino acid sequence analysis.

For the purpose of the present invention, the term hK2 may include an intact hK2 polypeptide and a fragment of hK2 polypeptide. For example, in one embodiment of the present invention, the hK2 polypeptide contained in an hK2-PI6 complex of the present invention may be clipped at arginine 145 of the hK2 polypeptide sequence. Therefore, when an hK2-PI6 complex with the clipped hK2 is purified through a reducing polyacrylamide gel, the complex will contain PI-6 and a fragment of hK2 that is covalently attached to PI-6. Another clipped fragment which is not covalently attached to PI-6 will be separated from the complex under reducing and denaturing conditions. For example, in one embodiment, an hK2-PI6 complex may consist of PI-6 and the hK2 146–237 fragment. Such a complex has a molecular weight of about 50 kDa measured by a reducing polyacrylamide gel technique. It should be understood that the hK2 contained in the complex of the present invention may be clipped at other locations of the hK2 sequence. Therefore, for the purpose of the present invention, the term hK2 as used for an hK2-PI6 complex may include any hK2 fragment clipped at any position of intact hK2 as long as the clipped fragment is covalently attached to the PI-6 of the complex.

It is a discovery of the present invention that PI-6 exists in the prostate tumor. It is also a discovery of the present invention that the hK2-PI6 complex exists in prostate tumor at an elevated level. The level of the hK2-PI6 complex is elevated if the amount of the complex is higher than the amount of the complex that exists in normal or benign tissues.

The hK2-PI6 complex of the present invention may be isolated from a prostate tissue by methods described herein, i.e., by in vitro preparation pure or semi-purified proteins, and also by any other methods known to one skilled in the art for protein purifications. The purified hK2-PI6 complex may be used for antibody development. Accordingly, one aspect iof the present invention provides an antibody that is specifically immunoreactive with and binds to an hK2-PI6 complex of the present invention. The term "specifically immunoreactive" or "specific" as used herein indicates that the antibodies of the present invention only recognize and bind to hK2-PI6 complexes of the present invention, not the free hK2 or free PI-6.

An antibody which consists essentially of pooled monoclonal antibodies with different epitopic specificities, as well as distinct monoclonal antibody preparations, are provided. Monoclonal antibodies are made from an antigen containing a complex of the present invention or a portion of the complex of the present invention by methods well known in the art (E. Harlow et al., *Antibodies. A Laboratory Manual*, Cold Spring Harbor Laboratory, 1988). In general, this method involves preparing an antibody-producing fused cell line, e.g., from primary spleen cells fused with a compatible continuous line of myeloma cells, growing the fused cells either in mass culture or in an animal species from which the myeloma cell line used was derived or is compatible. Such antibodies offer many advantages in comparison to those produced by inoculation of animals, as they are highly specific and sensitive and relatively "pure" immunochemically. Immunologically active fragments of antibodies are also within the scope of the present invention, e.g., the f(ab) fragment, as are partially humanized monoclonal antibodies.

If desired, polyclonal antibodies can be further purified, for example, by binding to and elution from a matrix to which a polypeptide or a peptide to which the antibodies were raised is bound. Those of skill in the art will know of various techniques common in the immunology arts for purification and /or concentration of polyclonal antibodies, as well as monoclonal antibodies. (See, for example, Coligan et al., Unit 9, Current Protocols in Immunology, Wiley Interscience, 1991, incorporated by reference.)

The term "antibody" as used in this invention includes intact molecules as well as fragments thereof, such as Fab, F(ab')$_2$ and Fv, which are capable of binding the epitopic determinant. These antibody fragments retain some ability to selectively bind with its antigen or receptor and are defined as follows:

(1) Fab, the fragment which contains a monovalent antigen-binding fragment of an antibody molecule, can be produced by digestion of the whole antibody with the enzyme papain to yield an intact light chain and a portion of one heavy chain;

(2) Fab', the fragment of an antibody molecule, can be obtained by treating the hole antibody with pepsin, followed by reduction, to yield an intact light chain and a ortion of the heavy chain—two Fab' fragments are obtained per antibody molecule;

(3) F(ab')$_2$, the fragment of the antibody that can be obtained by treating the hole antibody with the enzyme pepsin without subsequent reduction —F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA" ), defined as a genetically engineered molecule containing the variable region of the light chain, the variable region of the heavy chain, linked by a suitable polypeptide linker as a genetically fused single chain molecule.

Methods of making these fragments are known in the art. (See, for example, Harlow and Lane, *Antibodies: A Laboratory Manual*, Cold Spring Harbor Laboratory, New York (1988), incorporated herein by reference.)

As used in this invention, the term "epitope" means any antigenic determinant on an antigen to which the paratope of an antibody binds. Epitopic determinants usually consist of chemically active surface groupings of molecules, such as amino acids or sugar side chains, and usually have specific three-dimensional structural characteristics, as well as specific charge characteristics.

Since hK2-PI6 complexes of the present invention are elevated in prostate cancer tissues, they may be used as a serum marker for detecting prostate cancer. They may also be used as an immunohistological marker to detect prostate cancer tissues. In accordance with the present invention, the hK2-PI6 complexes of the present invention may be detected in patient tissue samples by immunohistochemical and/or in patient fluid samples by in vitro immunoassay procedures. The determination of the complexes of the present invention in a patient sample is of significant diagnostic utility and may be an indicator of or correlate with the progression of a prostate cancer patient.

Immunohistochemical methods for the detection of antigens in patient tissue specimens are well known in the art and need not be described in detail herein. For example, methods for the immunohistochemical detection of antigens are generally described in Taylor, *Arch. Pathol. Lab. Med.* 102:113 (1978). Briefly, in the context of the present invention, a tissue specimen obtained from a patient suspected of having a prostate related problem is contacted with an antibody, preferably a monoclonal antibody, recognizing a complex of the present invention. The site at which the antibody is bound is thereafter determined by selective staining of the tissue specimen by standard immunohistochemical procedures.

In an alternative embodiment, antibodies that are specific for either hK2 or PI-6 are used for detecting and determining the hK2-PI6 complexes of the present invention in a tissue specimen. According to this embodiment, the immunohistochemical procedure includes the steps of:

(a) providing a first antibody that is specific for free hK2, a second antibody that is specific for PI-6, and a third antibody that recognizes and binds a hK2-PI6 complex of the present invention;

(b) contacting the first and second antibodies with the tissue specimen under a condition that all the free hk2 and free PI-6 are blocked by the first and the second antibodies respectively;

(c) contacting the third antibody with the tissue specimen under a condition that allows the third antibody to bind the hK2-PI6 complex contained in the tissue specimen to form a ternary complex comprising the antibody and the hK2-PI6 complex; and (d) detecting or determining the presence or amount of the ternary complex.

In accordance with embodiments of the present invention, the third antibody may be an antibody against hK2, which antibody recognizes and binds not only free hK2 but also the hK2-PI6 complex of the present invention. Alternatively, the third antibody may be an antibody against PI-6, which antibody recognizes and binds to not only free PI-6, but also the hK2-PI6 complex.

It should be understood that if the hK2-PI6 complex is a dominant hK2 complex in a sample, such as a prostate tissue sample, only antibodies that recognize free hK2 and antibodies that recognize both free hk2 and hK2 complexes may be used for the purpose of detecting the hk2-PI6 complex. In this case, it may not be necessary for the use of antibodies against PI-6.

Antibodies against hK2 or PI-6 may be generated by the methods described herein and by methods that are commonly known in the art, using hK2 or PI-6 as antigens. Antibodies that recognize only free hK2 or PI-6 are those that recognize epitopes that are blocked by the formation of hK2-PI6 complex. Antibodies that recognize both free hK2 or free PI-6 and a hK2-PI6 complex are those that recognize epitopes that are not blocked by the formation of hK2-PI6 complex. The characteristic of hK2 or PI-6 antibodies may be determined by Western blot or any other methods known to one skilled in the art.

In one embodiment of the present invention, the tissue specimen is a tissue specimen obtained from the prostate of a patient. The prostate tissue may be a normal prostate tissue, a cancer prostate tissue or a benign prostatic hyperplasia tissue.

The general methods of the in vitro detection of antigenic substances in patient fluid samples by immunoassay procedures are also well known in the art and require no repetition herein. For example, immunoassay procedures are generally described in Paterson et al., *Int. J. Can.* 37:659 (1986) and Burchell et al., *Int. J. Can.* 34:763 (1984). According to one embodiment of the present invention, an immunoassay for detecting the complex of the present invention in a biological sample comprises the steps of (a) contacting an amount of an agent which specifically binds to an hK2-PI6 complex to be detected with the sample under a condition that allows the formation of a ternary complex comprising the agent and the hK2-P16 complex, and (b) detecting or determining the presence or amount of the ternary complex as a measurement of the amount of the hK2-PI6 complex contained in the sample.

For the purpose of the present invention, the biological sample can be any human physiological fluid sample that contains hK2-PI6 complexes of the present invention. Examples of the human physiological fluid sample include, but are not limited to, serum, seminal plasma, urine and blood.

For the purpose of the present invention, both monoclonal antibodies and polyclonal antibodies may be used as long as such antibodies possess the requisite specificity for the antigen provided by the present invention. Preferably, monoclonal antibodies are used.

Monoclonal antibodies can be utilized in liquid phase or bound to a solid phase carrier. Monoclonal antibodies can be bound to many different carriers and used to determine hK2-PI6 complexes of the present invention. Examples of well-known carriers include glass, polystyrene, polypropylene, polyethylene, dextran, nylon, amylases, natural and modified celluloses, polyacrylamides, agaroses and magnetites. The nature of the carrier can be either soluble or insoluble for purposes of the invention. Examples of insoluble carriers include, but are not limited to, a bead and a microtiter plate. Those skilled in the art will know of other suitable carriers for binding monoclonal antibodies, or will be able to ascertain such by routine experimentation.

In addition, the monoclonal antibodies in these immunoassays can be detectably labeled in various ways. For example, monoclonal antibodies of the present invention can be coupled to low molecular weight haptens. These haptens can then be specifically detected by means of a second reaction. For example, it is common to use such haptens as biotin, which reacts with avidin, or dinitrophenyl, pyridoxal and fluorescein, which can react with specific anti-hapten antibodies. In addition, monoclonal antibodies of the present invention can also be coupled with a detectable label such as an enzyme, radioactive isotope, fluorescent compound or metal, chemiluminescent compound or bioluminescent compound. Furthermore, the binding of these labels to the desired molecule can be done using standard techniques common to those of ordinary skill in the art.

One of the ways in which the antibodies can be detectably labeled is by linking it to an enzyme. This enzyme, in turn, when later exposed to its substrate will react with the substrate in such a manner as to produce a chemical moiety which can be detected by, for example, spectrophotometric or fluorometric means (ELISA system). Examples of enzymes that can be used as detectable labels are horseradish peroxidase, malate dehydrogenase, staphylococcal nuclease, delta-5-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase, and acetylcholine esterase.

For increased sensitivity in the ELISA system, the procedures described can be modified using biotinylated antibodies reacting with avidin-peroxidase conjugates.

The amount of antigen can also be determined by labeling the antibody with a radioactive isotope. The presence of the radioactive isotope would then be determined by such means as the use of a gamma counter or a scintillation counter. Isotopes which are particularly useful are $^3$H, $^{125}$I, $^{123}$I, $^{32}$P, $^{35}$S, $^{14}$C, $^{51}$Cr, $^{36}$Cl, $^{57}$Co, $^{58}$Co, $^{59}$Fe, $^{75}$Se, $^{111}$In, $^{99}$mTc, $^{67}$Ga, and $^{90}$Y.

Determination of the antigen is also possible by labeling the antibody with a fluorescent compound. When the fluorescently labeled molecule is exposed to light of the proper wave length, its presence can then be detected due to fluorescence of the dye. Among the most important fluorescent labeling compounds are fluorescein isothiocyanate, rhodamine, phycoerythrin, phycocyanin, allophycocyanin, o-phthaldehyde, and fluorescamine.

Fluorescence emitting metal atoms such as Eu (europium), and other lanthanides, can also be used. These can be attached to the desired molecule by means of metal-chelating groups, such as DTPA or EDTA.

Another way in which the antibody can be detectably labeled is by coupling it to a chemiluminescent compound.

The presence of the chemiluminescent-tagged immunoglobulin is then determined by detecting the presence of luminescence that arises during the course of a chemical reaction. Examples of particularly useful chemiluminescent labeling compounds are luminol, isoluminol, aromatic acridinium ester, imidazole, acridinium salt, and oxalate ester.

Likewise, a bioluminescent compound may also be used as a label. Bioluminescence is a special type of chemiluminescence which is found in biological systems and in which a catalytic protein increases the efficiency of the chemiluminescent reaction. The presence of a bioluminescent molecule would be determined by detecting the presence of luminescence. Important bioluminescent compounds for purposes of labeling are luciferin, luciferase, and aequorin.

Qualitative and/or quantitative determinations of hK2-PI6 complexes of the present invention in a sample may be accomplished by competitive or non-competitive immunoassay procedures in either a direct or indirect format. Examples of such immunoassays are the radioimmunoassay (RIA) and the sandwich (immunometric) assay. Detection of the antigens using the monoclonal antibodies of the present invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "immunometric assay" or "sandwich immunoassay" includes a simultaneous sandwich, forward sandwich and reverse sandwich immunoassay. These terms are well understood by those skilled in the art. Those of skill will also appreciate that antibodies according to the present invention will be useful in other variations and forms of assays which are presently known or which may be developed in the future. These are intended to be included within the scope of the present invention.

In accordance with one embodiment of the present invention, antibodies that are specific for free hK2 or PI-6 may also be used in an immunoassay of the present invention for detecting or determining in a sample of a human physiological fluid the hK2-PI6 complex of the present invention. For example, antibodies against hK2 or PI-6 may be used in a sandwich assay of the present invention. Accordingly, one embodiment of the present invention provides an immunoassay for detecting hK2-PI6 complexes in a sample, the assay including the steps of:

(a) providing a first antibody that recognizes one epitope of the hK2-PI6 complex, and a second antibody that recognizes another epitope of the hK2-PI6 complex, (b) contacting the first antibody with the sample under a condition that allows the first antibody to bind to the complex to form a first complex that comprises the first antibody and the hK2-PI6 complex, (c) contacting the second antibody with the first complex under a condition that allows the second antibody to bind to the hK2-PI6 complex to form a second complex that comprises the first antibody, the second antibody and the hK2-PI6 complex, and (d) detecting and determining the second complex as a measurement of the hK2-PI6 complex contained in the sample.

The first and second antibodies may be antibodies that are specifically immunoreactive with hK2-PI6 complexes of the present invention. Alternatively, the first antibody may be an antibody that is specific for hK2, and the second antibody may be an antibody that is specific for PI-6, or vise versa. Preferably, one of the first and second antibodies is bound to a solid support whereas another antibody is labeled with a detecting or detectable label by methods described herein. One skilled in the art should be able to design a proper sandwich assay without undue experimentation by using antibodies specific for hK2-PI6 complexes of the present invention or antibodies against hK2 and PI-6 in view of the teachings of the present invention.

One aspect of the present invention provides a diagnostic kit for detecting or determining in a sample a complex consisting of PI-6 and hK2. The kit comprises a known amount of an agent which specifically binds to the complex, wherein the agent is detectably labeled or binds to a detectable label. For the purpose of the present invention, the sample may be a sample of human physiological fluid such as, but not limited to, serum, seminal plasma, urine and blood. The sample may also be a tissue specimen coming from the prostate of a patient. The agent may be an antibody that specifically binds to hK2-PI6 complexes of the present invention. Preferably the agent is a monoclonal antibody, although a polyclonal antibody may also be used.

In another embodiment of the present invention, a diagnostic kit may comprise two known amounts of agents, wherein one agent recognizes one epitope of the hK2-PI6 complex, and another agent recognizes a different epitope of the hK2-PI6 complex. Preferably, one agent is labeled with a detectable label, and the another agent is bound to a solid support. In one embodiment of the present invention, both agents comprise respectively an antibody that is specifically immunoreactive to an hK2-PI6 complex of the present invention. In another embodiment of the present invention, one agent comprises an antibody that is specific for hK2, and the another agent comprises an antibody that is specific for PI-6.

Another aspect of the present invention provides a diagnostic method for determining the presence or absence of prostate cancer. The method includes the steps of:

(a) contacting an amount of an agent, which specifically binds to a complex consisting of PI-6 and hK2, with a sample obtained from a human containing the complex under a condition sufficient to allow the formation of a ternary complex comprising the agent, the PI-6, and the hK2, and (b) determining the amount of the ternary complex in the sample and correlating the amount of the ternary complex to the presence or absence of prostate cancer in the human.

In one embodiment of the present invention, the sample may be a sample of human physiological fluid including, but not limited to, serum, seminal plasma, urine, and blood. In another embodiment of the present invention, the sample may be tissue specimen from the prostate of a patient. For the purpose of the present invention, the agent may be an antibody that specifically recognizes hK2-PI6 complexes of the present invention. The antibody may be a monoclonal antibody or a polyclonal antibody.

It is a discovery of the present invention that PI-6 exists in prostate cancer tissues. It is also a discovery of the present invention that PI-6 exists at an elevated level as a complex with hK2 in prostate cancer. It is thus possible that PI-6 or some specific form of complexed PI-6 may show a correlation with prostate cancer. Therefore, the detection and measurement of PI-6 or a specific form of complexed PI-6 may be important in determining the existence of cancer in prostate or other tissue samples. For example, PI-6 may be used as an immunohistological marker to detect prostate cancer tissues. PI-6 of the present invention may be detected in patient tissue samples by immunohistochemical procedures that are described herein.

Accordingly, one aspect of the present invention provides a diagnostic method for determining the presence or absence of prostate cancer, the method comprising the steps of:

(a) contacting an amount of an agent, which specifically binds to PI-6, with a sample obtained from a human containing the PI-6 under a condition that allows the formation of a binary complex comprising the agent and the PI-6; and (b) determining the amount of the complex in the sample and correlating the amount of the complex to the presence or absence of prostate cancer in the human.

For the purpose of the present invention, the sample may be a sample from a prostate or other tissue. In one embodiment, the agent comprises an antibody that is specific for PI-6.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLE I

Characterization of hK2-PI6 Complexes in Prostate Tissue

Material and Methods

Material

PAI-1 was obtained from Oncogene Research Products (San Diego, Calif.). ACT was obtained from Athens Research (Athens, Ga.). Purified Recombinant hK2 were expressed in the syrian hamster carcinoma cell line, AV12, and immunoaffinity purified using the murine hK2-specific monoclonal antibody HK1G586. 1 as described previously (14; 25). HK1G586. 1 has been shown to have negligible cross-reactivity with PSA (18; 26). PF1D215 is a monoclonal developed toward PSA fragments, but which is also cross-reactive with hK2. PSM 773 is a mAb which specific for PSA and does not cross react with hK2. The above antibodies were developed at Hybritech (San Diego, Calif.).

Methods

Extraction and SDS PAGE of Prostate Tissues

Prostatectomy tissues were frozen in liquid nitrogen, pulverized, then homogenized in PBS buffer containing a cocktail of protease inhibitors (Complete, Boeringer Manheim). SDS PAGE was performed on a Novex mini-gel with 4–20% gradient. Each lane was loaded with the extraction supernatant solution which contained 5 ug of total protein. Samples were electroblotted onto nitrocellulose for Western blot analysis and PVDF for N-terminal sequencing. Primary antibodies HK1G586.1 and PF1D215.2 were used at 5 ug/ml and secondary antibody (Goat anti-mouse-FW, 1:50,000, Jackson Immunoresearch Laboratories, Inc., West Grove, Pa.) was used to probe the blots. The immunoreactive signals were detected by ECL Ultra (Amersham, Buckinghamshire, England) according to manufacturer's instructions.

Preparation of hK2-complex Standards

In vitro complexes of hK2 with ACT, PCI and PAI-1 were prepared by incubation of hK2 with excess inhibitor as described previously (17).

N-terminal Sequence Analysis

N-terminal analysis was performed on a PE-Applied Biosystems Model 492 amino acid sequencer. Protein bands blotted onto PVDF were visualized by Coomassie Brilliant Blue R-250, excised and applied to the sequencer.

Samples for internal sequencing were first reduced with 2 mm DTT and alkylated with iodoacetamide prior to SDS-PAGE. Coomassie-stained bands from the gel were excised, cut into small pieces, washed 2× with 50% acetonitrile/0,2M sodium bicarbonate for 30 min, and completely dried in a speedvac. Dried gel slices were then reconstituted with 50 ul 0,2 M sodium bicarbonate containing 1 ug of sequencing grade trypsin (Promega). Samples were digested for 20 h at 37° C.

Results

Benign and cancerous prostate tissues were homogenized and extracted. The supernatant solutions were subjected to non-reducing SDS-PAGE and analyzed by Western blot (FIG. 1). FIG. 1, lanes 1 and 2 were probed with the hK2-specific monoclonal antibody, hK1G586. 1, and shows the free and complexed hK2 present in benign prostate tissue and tumor, respectively. The band at 33K is hK2 and the band at 64K indicates a complex of hK2. The level of complexed hK2 is higher in the tumor extract. The mobility of this complex indicates a molecular mass of 64 kDa, lower than the known physiological hK2 complexes of ACT and PCI (see FIG. 2).

Lanes 3 and 4 were probed with PSM773 to detect PSA and PSA complexes. No detectable higher molecular mass PSA complex was observed even after extended exposure times. Immunoassay measurements of the hK2 and PSA in these extracts gave a similar value for benign tissue and tumor. Total PSA was approximately 10 ug per mg protein and total hK2 was 0.3 ug per mg protein. 5 ug of total protein was loaded in each lane. Thus, significant levels of hK2 are found as a complex in prostate tissue, and this complex is elevated in prostate tumor. In contrast, the much higher levels of PSA are predominantly in the free, uncomplexed form. FIG. 1 further indicates that the 64 kDa hK2-complex is the major kallikrein complex found in prostate tissue extracts.

Figure 2:
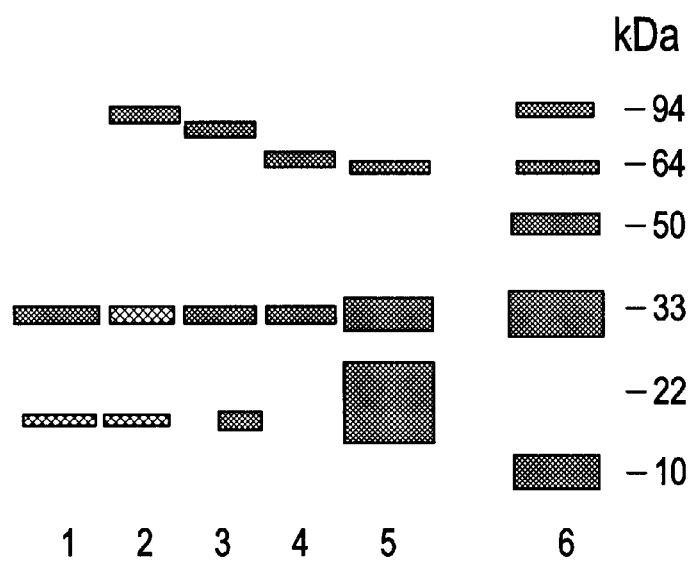
FIG. 2 shows a Western blot of hK2-complex standards and prostate tissue extract.

In order to obtain enough material to identify the inhibitor in the hK2-complex, approximately 50 g of prostate tissue was extracted. The hK2 and hK2-complex were purified from the extract by passage over an immunoaffinity column containing the hK2-specific monoclonal antibody, HK1G586.1. FIG. 2 shows the Western blot profile of the purified hK2 forms eluted from the affinity column together with hK2-complex standards prepared in vitro. Lane 1 shows purified recombinant hK2 and lanes 2, 3 and 4 contain hK2 complexes with ACT, PCI and PAI-1, respectively. The mobilities of these hK2 complexes are different due to the differences in the molecular mass of the inhibitors. For example, lane 2 is hK2 incubated with ACT which forms a 90 kDa complex; lane 3 is hK2 incubated with PCI which forms a 75 kDa complex; lane 4 is hK2 incubated with PAI-1 which forms a 66 kDa complex.

Lane 5 shows the purified hK2 forms extracted from the tissue. When probed with HK1G586. 1 a faint band at 64 kDa is detected, together with strong bands at 33 kDa and 22 kDa. The 22 kDa is commonly present in hK2 preparations and can be seen as faint bands in the standard hK2 samples in lanes 1–4. This band is a fragment of hK2 which results from a cleavage at arginine 145. The epitope for HK1G586.1 is thus shown to be on the N-terminal side of this clip.

Lane 6 is the same as lane 5 except that this lane was probed with PF1D215. PF1D215 was developed towards fragments of PSA but is cross-reactive with hK2. Lane 6 shows a different banding pattern than lane 4. Both the 30 kDa and the faint 64 kDa band are detected, but 2 new major bands at 10 kDa and 50 kDa are detected. A faint band migrating at the same position as hK2-ACT is also detected.

Figures 3, 5:
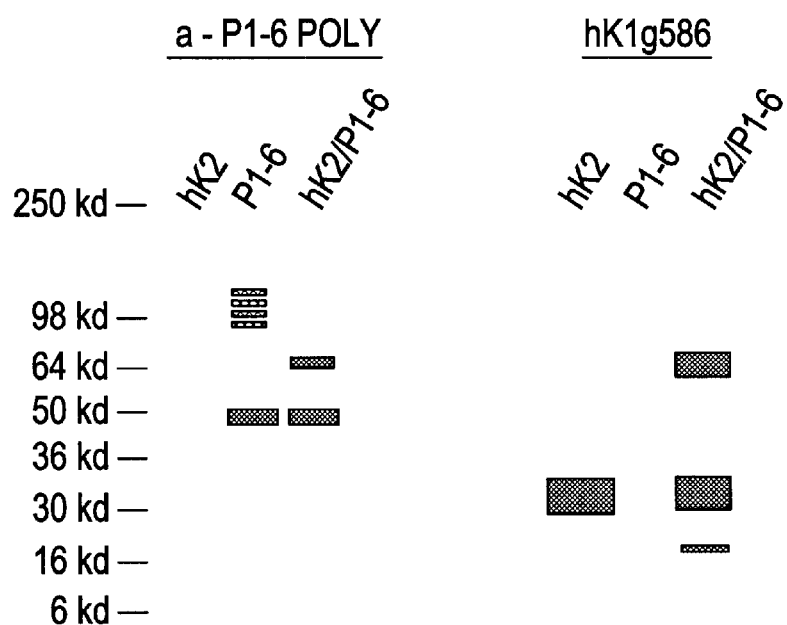
FIG. 3 shows N-terminal sequence of a blot of purified hK2 forms from prostate tissues.
FIG. 5 is a Western blot of hK2-PI6 complex formed in vitro, as detected with the rabbit anti-PI-6 polyclonal antibody of the present invention and hK2 antibody.

The identity of the bands in FIG. 2 were determined by N-terminal sequencing a blot of the same sample. In FIG. 3, 15 uL of the concentrated, purified tissue hK2 containing approximately 10 ug of free hK2 was loaded in this lane. Each band on PVDF was excised and subjected to N-terminal sequencing through nine cycles. Bands 1 and 2 are hK2 fragments of hK2. Band 1 begins with the sequence, SLQCVSLHL, identified as SEQ ID NO:1, which corresponds to the hK2 sequence beginning at serine 146. Together with the molecular mass of 10 kDa, this indicates that this fragment is hK2 146–237. Band 2 begins with the N-terminal sequence for hK2 and is consistent with the hK2 fragment from residues 1–145. Band 3, at 33 kDa, also begins with the N-terminal sequence which is consistent with intact hK2.

Band 4, the 50 kDa band seen in FIG. 2, lane 6, begins with the sequence SLQCVSLHL, identified as SEQ ID NO:1. This is the same sequence as band 1, suggesting that this is the 10 kDa fragment of hK2 covalently attached to the inhibitor. However, the absence of a second sequence indicated that that N-terminus of the inhibitor was blocked. The reactive serine in hK2 which forms the covalent bond with serpins is residue 189, which is C-terminal to the 145 clip. This is consistent with FIG. 2, lane 6, where PF1D215.2 was shown to recognize the 10 kDa fragment of hK2 146–237, and to detect the 50 kDa complex consisting of the hK2 146–237 covalently attached to the inhibitor.

Band 5, corresponding to the faint 64 kDa band in FIG. 2, contained the hK2 N-terminus sequence. Since this molecular mass is higher than intact hK2, it is likely that this band contains intact hK2 attached to a blocked inhibitor. The stronger band just above band 5 was determined to be human serum albumin by sequencing. And finally, band 6 had two sequences: intact hK2 and ACT, which indicates that this is intact hK2 bound to ACT.

The sequences in FIG. 3 indicate that the vast majority of the hK2 is clipped at arginine 145 and that the majority of the hK2 bound to the blocked inhibitor (at 50 kDa) is also clipped. The relative percentage of hK2 in each band was calculated, based on the total pmol of all bands measured during sequence analysis. Band 1 contained 48 pmoles of the 10 kDa hK2 fragment which represented 73% of the total hK2 sequenced on this blot. Band 2, the 22 kDa fragment, contained 84% or 11% higher hK2 than band 1. The additional 22 kDa hK2 fragment was presumably derived from the clipped hK2 complex at 50 kDa, since only the 10 kDa fragment remains bound to the inhibitor. In summary, sequence analysis of the blot shows that about 73% of the hK2 is clipped at Arg145, 13% is intact hK2, ~11% is bound to the blocked inhibitor and ~2% is in a complex with ACT.

Figure 4:
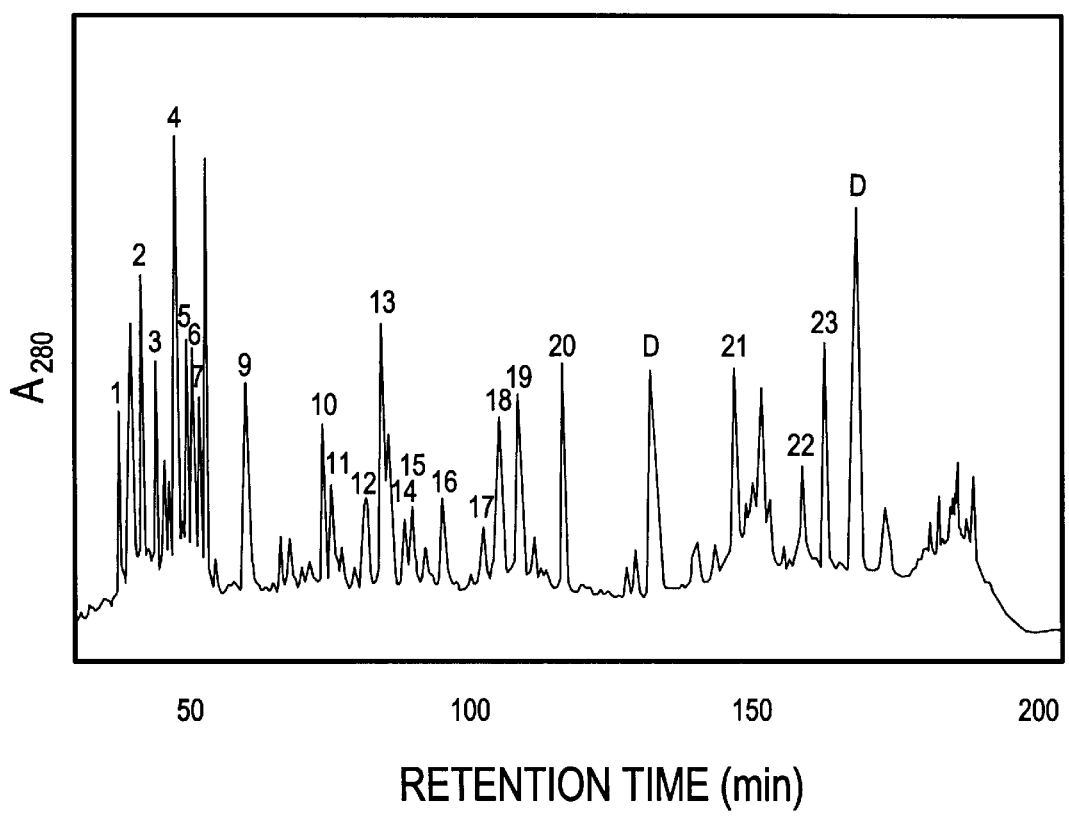
FIG. 4 is the reversed phase HPLC profile of the peptides generated after trypsin digestion of the 50 kDa hK2-PI6 band excised from a gel.

Since the blocked inhibitor was present in complex with both the intact (64 kDa) and the clipped fragment of hK2 (50 kDa), it was necessary digest the complex with trypsin and sequence the internal peptide fragments to establish the identity of the inhibitor. Three lanes of purified tissue hK2 identical to FIG. 3 were run and the 50 kDa bands excised from the SDS-PAGE and digested with trypsin. The tryptic fragments were then separated by the capillary C18 reversed-phase HIPLC microblotter and automatically blotted onto PVDF. The chromatogram showing the resolution of the tryptic digest of the 50 kDa band is seen in FIG. 4. Each of the indicated peaks was sequenced. A database search of the internal sequences revealed that the other protein present at 50 kDa was a serine protease inhibitor designated Protease Inhibitor-6, PI6. A total of 24 peptide fragments of PI6 were positively identified, comprising more than 70% of the total PI-6 protein mass. As expected, no peptide fragments of the PI-6 blocked N-terminus, or the fragments after the PI-6 residue 341 reactive site were detected. HK2 fragments were identified in peaks 2, 5, 15, 18, and 19. This represents five of the 7 possible tryptic fragments of hK2 145–237. No tryptic fragments from the hK2 1–145 region were found, consistent with the sequence information for the 50 kDa band in FIG. 3. No unidentified sequences were detected.

Discussion

These results demonstrate the presence of a novel prostatic complex between hK2 and the cytoplasmic serine protease inhibitor, PI-6. This is the first evidence of a tissue-specific inhibitor of hK2 and has implications for the regulation of hK2 activity and function in the prostate. It is equally compelling that the inhibitor is identified as PI-6, a relatively newly discovered cytoplasmic inhibitor which has not been reported in association with a cancer-related protease.

FIG. 3 indicates that hK2-PI6 represents approximately 10% of the endogenous hK2. FIG. 1 shows hK2-PI6 to be elevated in tumor over benign tissue.

The finding of a tissue inhibitor of hK2 is important since hK2 has been shown to be highly correlated with prostate cancer. hK2 is elevated in the serum of prostate cancer patients. hK2 is elevated in the epithelium of poorly differentiated prostate tissue compared to benign tissues. hK2 has been shown to activate urokinase-type plasminogen activator, and to inactivate plasminogen activator inhibitor-1. hK2 cleaves and inactivates IGFB3, thus providing an enhanced environment for metastatic cell growth. hK2 may be involved in the activation of PSA.

The reasons for the interaction of hK2 and PI-6 are less clear. hK2 has been shown to be secreted by LNCaP cells and is therefore thought to be an extracellular protease. The reaction between hK2 and PI-6 may therefore result from abnormal intracellular hK2 activation as part of a defective oncolytic pathway or the leakage of PI-6 from damaged or necrotic neoplastic tissue. In either case the presence of hK2-PI6 may well prove to be a valuable marker for the detection of prostate cancer.

It should be noted that hK2-PI6 was not detected in normal seminal plasma (data not shown), indicating that this inhibitor is tissue specific and is not part of the normal pathway of PSA and hK2 secretion into the glandular lumen of the prostate. It is possible that seminal levels of hK2-PI6 may become detectable in patients with prostate cancer.

FIGS. 2 and 3 indicate that 75% of the hK2 in these tissues is clipped at arginine 145. For accurate assessment of the 64 kDa complex in crude extracts analyzed by Western blot it was necessary to run gels under non-reducing conditions, as in FIG. 1, to maintain the hK2 intact as a single 33 kDa polypeptide held together by disulfide bonds. The reactive serine in hK2 which forms the covalent bond with serpins is residue 189, which is C-terminal to the 145 clip. In FIG. 2, lane 5, PF1D215.1 was shown to recognize the 10 kDa fragment of hK2 146–237, and to detect the 50 kDa PI-6 complex consisting of the hK2 146–237 covalently attached to PI-6. PF1D215 was only used on immunoaffinity purified hK2 since this monoclonal antibody would otherwise cross-react with the 20 to 50-fold higher levels of PSA in crude tissue extracts.

Since clipped hK2 has been shown to be inactive it is likely that the hK2-PI6 complex formed prior to cleavage. PSA, which contains a similarly susceptible site at residue 145, showed negligible cleavage by Western blot under reducing conditions (data not shown).

The observation that hK2 is largely clipped has previously been described in seminal plasma and prostate tissue extracts (19). Minor levels of higher molecular mass forms of hK2 were detected in the tissue extracts but were not identified in those studies.

The finding of an hK2-PI6 complex is intriguing not only for the presence of hK2, but the identification of PI-6. PI-6 has homology to other serpins members of the ovalbumin family such as antithrombin III, PAI-1, PAI-2, maspin etc (20; 27). It is present in a number of tissues including human placenta, kidney, heart, skeletal tissue and platelets. PI-6 has been shown to be cytoplasmically localized and so its most likely physiological role would be expected to be intracellular protection against internal proteolytic damage.

However, no specific role or endogenous protease complex has been identified. Unlike PAI-2 which can function as an intracellular protease inhibitor but can also be secreted as an extracellular inhibitor, PI-6 appears to be exclusively intracellular. Attempts to engineer a promoter to force secretion of PI-6 rendered it inactive, possibly due to glycosylation (21).

PI-6 strongly inhibits trypsin, urokinase and factor 11 and has also been shown to have inhibitory activity towards chymotrypsin-like proteases (28). In the current study the chymotrypsin-like PSA did not, however, show evidence of complex with PI-6 in tissue extracts.

EXAMPLE II

Characterization of PI-6 In Prostate Tissues

A number of questions are raised by this study, which relate to both hK2 and PI-6. Is the level of PI-6 itself variable in tumor compared to benign tissue and is this inhibitor correlated with oncogenic development. To answer these questions, PI-6 antibodies were developed and PI-6 expression in tumor versus benign or normal tissues were compared. This study may be useful in correlating these findings to the staging and patient outcomes.

Materials and Methods

Expression and Purification of PI-6

BL2Ide3 cells transformed with PNID were grown in LB+Kanamycin (30 ug/ml) till $OD_{600}$=0.7, then induced with 1 mM IPTG for two hours. The cells were harvested by centrifugation at 5K (JA 14) for 10 minutes (NB 9347: 88).

The cell pellet from 500 ml of *E.coli* culture was resuspended in 20 ml sonicate buffer (300 nM NaCl, 50 mM Sodium Phosphate pH8.0, 2 mM B-Mercaptoethanol) plus protease inhibitor cocktail. The resuspended cells were sonicated 4 times for 15 seconds. The supernatant and cell debris were separated by centrifugation at 9K (JA 20) for 20 minutes.

The supernatant was incubated with 5 ml prewashed (with sonicate buffer) Cobalt resin at 4° C. for 30 minutes. The resin was collected by centrifugation at 2K (JA 20) for 5 minutes. The resin was then washed with 20 ml of the wash buffer (300 mM NaCl, 50 mM Sodium Phosphate pH 6.0, 10% glycerol, 2 mM 2-Mercaptoethanol) three times, each time shaken at 4° C. for 20 minutes, then collected with centrifugation. PI-6 was eluted twice with the wash buffer plus 400 mM Imidazole. The supernatant was collected by centrifugation at 2K (JA20) for 5 minutes after shaking at 4° C. for 20 minutes.

All the fractions from the expression and purification were checked on SDS gel. It seems the majority of the expressed PI-6 is insoluble. The soluble fraction was about 90% purified by Cobalt resin. The purified protein was dialyzed against PBS plus 2 mM B-mercaptoethanol. The concentration of the purified PI-6 was measured by Chemi Imager Analysis based on the density comparison with the lyophilized PI-6. The yield from the 500 ml *E.coli* culture was about 1 mg.

The pellet after sonication was washed with 1% Triton X-100, 1M NaCl, and 8M Urea sequentially. The insoluble fraction was only soluble in 8M Urea.

Generating Antibodies Against PI-6

The α-PI-6 polyclonal antibody (α-PI-6) was generated by injecting rabbit with the purified PI-6 by using methods that are commonly known to one skilled in the art.

hK2/PI-6 Complex Formation

1. Materials used:
   pure hK2: 10 ng/ul
   PI-6: 180 ng/ul purified from *E.coli*

2. Reaction set up:
   6 ul pure hK2 (30 ng)+14 ul PBS
   6 ul PI-6 (540 ng)+14 ul PBS
   6 ul PI-6 (540 ng)+6 ul pure hK2 (30 ng)+8 ul PBS The reactions were incubated at room temperature for one hour, then 20 ul of loading buffer was added to each of them. The reactions were then boiled for three minutes and loaded in duplicate of 20 ul each on the 4–20% SDS gel. Western blotting followed and HK1G568.1 (5 ug/ml) or α-PI-6 (2 ug/ml) were used as primary antibodies. The secondary antibodies for both sets were diluted 1:5,000.

Results

FIG. 5 is a Western blot of hK2-PI6 complex formed in vitro with α-PI-6 antibody of the present invention and hK2 antibody. This figure shows that purified PI-6 formed a complex with purified hK2. This complex was recognized by both α-PI-6 polyclonal and α-hK2 monoclonal (HK1G586. 1) antibodies. PI-6 did not complex with the zymogen, enzymatically inactive form of hK2 (data not shown).

Figure 6:
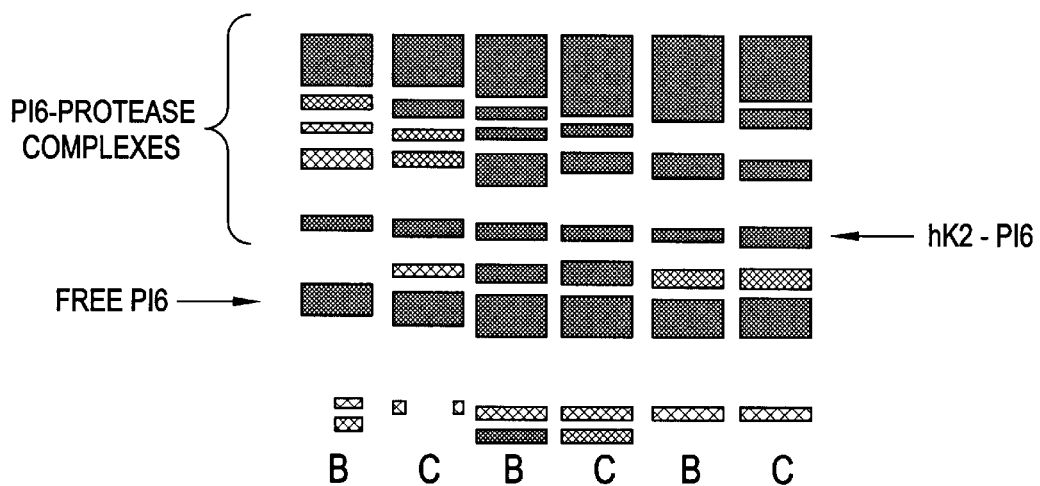
FIG. 6 shows a Western blot of prostate tissue extracts probed with the rabbit anti-PI-6 polyclonal antibody of the present invention.

FIG. 6 shows a Western blot of prostate tissue extracts probed with the α-PI-6. The α-PI-6 antibody was generated by immunization of rabbits with *E.coli*-expressed PI-6. Both benign (B) and cancer tissue (C) extracts were obtained from three different tissues. The Western blot shows that the α-PI-6 antibody recognized not only PI-6, but also hK2-PI6 complex, and other apparent complexes of PI-6. The Western blot also shows that the level of hK2-PI6 complex is higher in cancer than in the benign tissues.

The large band at the lower portion of the gel is consistent with the molecular weight of free PI-6. This gel demonstrated that PI-6 is present in prostate tissue in significant levels, and that it appears to be in complex with several other proteins. The fact that the level of hK2-PI6 complex is higher in cancer tissue than benign tissue indicates that PI-6 may be playing a role in the regulation of some processes associated with cancer development.

Figure 7:
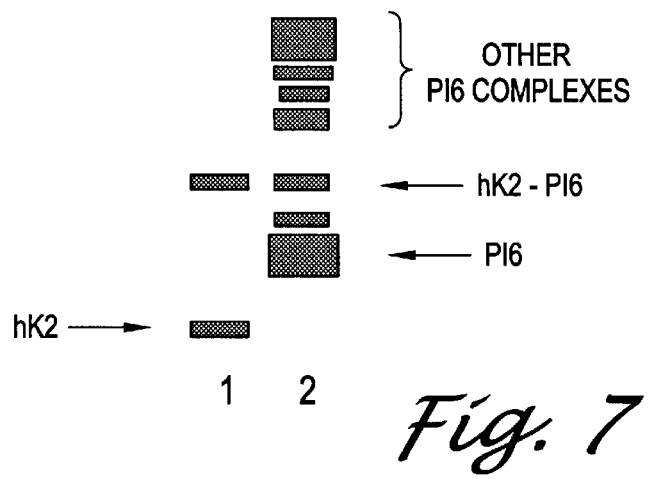
FIG. 7 shows the hK2-PI6 complex in prostate tissue extracts as detected by the rabbit polyclonal anti-PI-6 antibody of the present invention, and also as detected with anti-hK2 antibody.

FIG. 7 shows a Western blot of a prostate tissue extract. Lane 1 was probed with HK1G586.1 to detect hK2 forms. In lane 1 the free hK2 and the 64 kDa complex is seen, similar to FIG. 1. Lane 2 was probed with the α-PI-6 antibody. In lane 2 the free PI-6 is detected at approximately 42 kDa and an equivalent amount of hK2-PI6 complex is seen at exactly the same 64 kDa mobility as seen with the anti-hK2 antibody.

Again, it is a discovery of the present invention that PI-6 is present in prostate tissues. It is also a discovery of the present invention that PI-6 may be associated with cancer. The discovery that PI-6 is complexed with an identified endogenous protease may suggest that PI-6 could be involved in an oncolytic process, either pro or con.

The foregoing is meant to illustrate, but not to limit, the scope of the invention. Indeed, those of ordinary skill in the art can readily envision and produce further embodiments, based on the teachings herein, without undue experimentation.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

Reference List

1. Berg, T., Bradshaw, R. A., Carretero, O. A., Chao, J., Chao, L., Clements, J. A., Fahnestock, M., Fritz, H., 1. Gauthier, F., MacDonalds, R. J., Margolius, H. S., Morris, B. J., Richards, R. I., and Scicli, A. G. A common nomenclature for members of the tissue (glandular) kallikrein gene families. Agents Actions Suppl., 38: 19–25, 1992.
2. Rittenhouse, H. G., Finlay, J. A., Mikolajczyk, S. D., and Partin, A. W. Human kallikrein 2 (hK2) and prostate-specific antigen (PSA): Two closely related, but distinct, kallikreins in the prostate. Crit Rev Clin Lab Sci, 35: 275–368, 1998.
3. Chapdelaine, P., Paradis, G., Tremblay, R., and Dube, J. High level of expression in the prostate of a human glandular kallikrein MRNA related to prostate-specific antigen. FEBS Lett., 236: 205–208, 1988.
4. Morris, B. J. A kallikrein gene expressed in human prostate. Clin.Exp.Pharm.Phys., 16: 345–351, 1989.
5. Bridon, D. and Dowell, B. Structural comparison of prostate-specific antigen and human glandular kallikrein using molecular modeling. Urology, 45: 801–806, 1995.
6. Vihinen, M. Modeling of prostate specific antigen and human glandular kallikrein structures. BBRC, 204: 1251–1256, 1994.
7. Young, C. Y., Andrews, P. E., Montgomery, B. T., and Tindall, D. J. Tissue-specific and hormonal regulation of human prostate-specific glandular kallikrein. Biochemistry, 31: 818–824, 1992.
8. Clements, J. The glandular kallikrein family of enzymes: tissue specific expression and hormonal regulation. Endocrine Rev., 10: 393–419, 1989.
9. Deperthes, D., Marceau, F., Frenette, G., Lazure, C., Tremblay, R. R., and Dube, J. Y. Human kallikrein hK2 has low kininogenase activity while prostate- specific antigen (hK3) has none. Biochim Biophys Acta, 1343: 102–106, 1997.
10. Bourgeois, L., Brillard-Bourdet, M., Deperthes, D., Juliano, M. A., Juliano, L., Tremblay, R. R., Dube, J. Y., and Gauthier, F. Serpin-derived peptide substrates for investigating the substrate specificity of human tissue kallikreins hK1 and hK2. J Biol Chem, 272: 29590–29595, 1997.
11. Kumar, A., Mikolajczyk, S. D., Goel, A. S., Millar, L. S., and Saedi, M. S. Expression of pro form of Prostate-specific antigen by mammalian cells and its conversion to mature, active form by human kallikrein 2. Cancer Res., in press: 1997.
12. Takayama, T. K., Fujikawa, K., and Davie, E. W. Characterization of the precursor of prostate-specific antigen-activation by trypsin and by human glandular kallikrein. J.Biol.Chem., 272: 21582–21588, 1997.
13. Lovgren, J., Rajakoski, K., Karp, M., Lundwall, A., and Lilja, H. Activation of the zymogen form of prostate-specific antigen by human glandular kallikrein 2. Biochem.Biophys.Res.Comm., 238: 549–555, 1997.
14. Mikolajczyk, S. D., Millar, L. S., Marker, K. M., Grauer, L. S., Goel, A. S., Cass, M. M. J., Kumar, A., and Saedi, M. S. Ala217 is important for the catalytic function and autoactivation of prostate-specific human kallikrein 2. Eur.J.Biochem., 246: 440–446, 1997.
15. Darson, M. F., Parcelli, A., Roche, P., Rittenhouse, H. G., Wolfert, R. L., Young, C. Y. F., Klee, G. G., Tindall, D. J., and Bostwick, D. G. Human Glandular Kallikrein 2 (hK2) expression in prostatic intraepithelial neoplasia and adenocarcinoma: a novel inprostate cancer marker. Urology, 49(6): 857–862, 1997.
16. Frenette, G., Tremblay, R. R., Lazure, C., and Dube, J. Y. Prostatic kallikrein (hk2), but not prostate-specific antigen (hk3), activates single-chain urokinase-type plasminogen activator. Int.J.Cancer, 71: 897–899, 1997.
17. Mikolajczyk, S. D., Millar, L. S., Kumar, A., and Saedi, M. S. Human kallikrein 2 (hK2) inactivates and complexes with plasminogen activator inhibitor-1 (PAI-1). Int J Cancer, In press: 1999.
18. Grauer, L. S., Finlay, J. A., Mikolajczyk, S. D., Pusateri, K. D., and Wolfert, R. L. Detection of human glandular kallikrein, hK2, as its precursor form and in complex with protease inhibitors in prostate carcinoma serum. J Androl, 19: 407–411, 1998.
19. Deperthes, D., Chapdelaine, P., Tremblay, R. R., Brunet, C., Berton, J., Hebert, J., Lazure, C., and Dube, J. Y. Isolation of prostatic kallikrein hK2, also known as hGK-1, in human seminal plasma. Biochim Biophys Acta, 1245: 311–316, 1995.
20. Morgenstern, K. A., Henzel, W. J., Baker, J. B., Wong, S., Pastuszyn, A., and Kisiel, W. Isolation and characterization of an intracellular serine proteinase inhibitor from a monkey kidney epithelial cell line. J Biol Chem, 268: 21560–21568, 1993.
21. Scott, F. L., Coughlin, P. B., Bird, C., Cerruti, L., Hayman, J. A., and Bird, P. Proteinase inhibitor 6 cannot be secreted, which suggests it is a new type of cellular serpin. J Biol Chem, 271: 1605–1612, 1996.
22. Morgenstern, K. A., Sprecher, C., Holth, L., Foster, D., Grant, F. J., Ching, A., and Kisiel, W. Complementary DNA cloning and kinetic characterization of a novel intracellular serine proteinase inhibitor: mechanism of action with trypsin and factor Xa as model proteinases. Biochemistry, 33: 3432–3441, 1994.
23. Riewald, M., Morgenstern, K. A., and Schleef, R. R. Identification and characterization of the cytoplasmic antiproteinase (CAP) in human platelets. Evidence for the interaction of CAP with endogenous platelet proteins. J Biol Chem, 271: 7160–7167, 1996.
24. Coughlin, P., Sun, J., Cerruti, L., Salem, H. H., and Bird, P. Cloning and molecular characterization of a human intracellular serine proteinase inhibitor. Proc Natl Acad Sci U S A, 90: 9417–9421, 1993.
25. Kumar, A., Goel, A., Hill, T., Mikolajczyk, S., Millar, L., Kuus-Reichel, K., and Saedi, M. Expression of human glandular kallikrein, hK2, in mammalian cells. Cancer Res., 56: 5397–5402, 1996.
26. Finlay, J. A., Evans, C. L., Day, J. R., Payne, J. K., Mikolajczyk, S. D., Millar, L. S., Kuus-Reichel, K., Wolfert, R. L., and Rittenhouse, H. G. Development of monoclonal antibodies specific for human glandular kallikrein (hK2): development of a dual antibody immunoassay for hK2 with negligible prostate-specific antigen cross-reactivity. Urology, 51: 804–809, 1998.
27. Sprecher, C. A., Morgenstern, K. A., Mathewes, S., Dahlen, J. R., Schrader, S. K., Foster, D. C., and Kisiel, W. Molecular cloning, expression, and partial characterization of two novel members of the ovalbumin family of serine proteinase inhibitors. J Biol Chem, 270: 29854–29861, 1995.
28. Riewald, M. and Schleef, R. R. Human cytoplasmic antiproteinase neutralizes rapidly and efficiently chymotrypsin and trypsin-like proteases utilizing distinct reactive site residues. J Biol Chem, 271: 14526–14532, 1996.

SUMMARY OF SEQUENCES

SEQ ID NO:1 is the amino acid sequence of the N-terminus of hK2.

What is claimed is:

1. An isolated and substantially pure complex consisting of protease inhibitor-6 (PI-6) and human kallikrein 2 (hK2).

2. The complex of claim 1, wherein the complex has a molecular weight of about 64 kDa by non-reducing polyacrylamide gel technique.

3. The complex of claim 1, wherein the complex has a molecular weight of about 50 kDa by reducing polyacrylamide gel technique.

4. The complex of claim 3, wherein hK2 is a fragment of hK2 consisting of amino acids 146–237.

5. The complex of claim 1 that is isolated from prostate tissue.

* * * * *

SEQUENCE LISTING

<160> NUMBER OF SEQ ID NOS: 1

<210> SEQ ID NO 1
<211> LENGTH: 9
<212> TYPE: PRT
<213> ORGANISM: Homo sapiens

<400> SEQUENCE: 1

Ser Leu Gln Cys Val Ser Leu His Leu
1               5